United States Patent
Piestun et al.

(10) Patent No.: US 12,379,312 B2
(45) Date of Patent: Aug. 5, 2025

(54) SYSTEMS AND METHODS FOR IMAGING AND CHARACTERIZING OBJECTS INCLUDING THE EYE USING NON-UNIFORM OR SPECKLE ILLUMINATION PATTERNS

(71) Applicants: The Regents of the University of Colorado, Denver, CO (US); Sorbonne Université, Paris (FR)

(72) Inventors: Rafael Piestun, Boulder, CO (US); Kristina Irsch, Paris (FR); Simon Labouesse, Boulder, CO (US); Sylvain Gigan, Paris (FR)

(73) Assignees: The Regents of the University of Colorado, Denver, CO (US); Sorbonne Université, Paris (FR)

( * ) Notice: Subject to any disclaimer, the term of this patent is extended or adjusted under 35 U.S.C. 154(b) by 610 days.

(21) Appl. No.: 17/765,364

(22) PCT Filed: Sep. 30, 2020

(86) PCT No.: PCT/US2020/053656
§ 371 (c)(1),
(2) Date: Mar. 30, 2022

(87) PCT Pub. No.: WO2021/067515
PCT Pub. Date: Apr. 8, 2021

(65) Prior Publication Data
US 2022/0390369 A1 Dec. 8, 2022

Related U.S. Application Data

(60) Provisional application No. 62/908,151, filed on Sep. 30, 2019.

(51) Int. Cl.
*G01N 21/47* (2006.01)
*A61B 5/00* (2006.01)
*G01N 21/64* (2006.01)

(52) U.S. Cl.
CPC .......... *G01N 21/47* (2013.01); *A61B 5/0084* (2013.01); *G01N 21/6456* (2013.01); *A61B 5/0066* (2013.01)

(58) Field of Classification Search
CPC .. G01N 21/47; G01N 21/6456; A61B 5/0084; A61B 5/0066; A61B 3/102; A61B 3/12; G02B 27/48
(Continued)

(56) References Cited

U.S. PATENT DOCUMENTS 6,142,629 A * 11/2000 Adel .................. G01J 3/2823
351/206
6,276,798 B1 * 8/2001 Gil ..................... G01J 3/502
351/206
(Continued)

FOREIGN PATENT DOCUMENTS

CN 107202780 A 9/2017

OTHER PUBLICATIONS

Ayuk, R. et al., "Structured Illumination Fluorescence Microscopy With Distorted Excitations Using A Filtered Blind-SIM Algorithm," Optics Letters, vol. 38, No. 22, pp. 4723-4726, Nov. 15, 2013.
International Application No. PCT/US2020/053656, International Search Report, Written Opinion, 14 pages, Feb. 5, 2021.

*Primary Examiner* — Mohammed A Hasan (57) ABSTRACT

Systems and methods are provided for imaging and characterizing objects including the eye using non-uniform or speckle illumination patterns. According to the present technology, a method for characterizing at least a portion of an object may include generating, using at least one light source, one or multiple non-uniform illumination patterns on
(Continued)

an object. The method may also include detecting, using a detector, backscattered light from the object in response to the generating. The method may further include extracting, using the detector, data representative of the backscattered light. The method may also include processing, using a processing unit, the data representative of the backscattered light to create one or more images of at least a portion of the object.

15 Claims, 8 Drawing Sheets

(58) Field of Classification Search
USPC .......................................................... 351/211
See application file for complete search history.

(56) References Cited

U.S. PATENT DOCUMENTS

| | | | |
|---|---|---|---|
| 6,657,796 B2 | 12/2003 | Greenberg | |
| 9,357,920 B2 | 6/2016 | Yates et al. | |
| 2003/0231285 A1* | 12/2003 | Ferguson | A61B 3/1025 351/221 |
| 2005/0254008 A1* | 11/2005 | Ferguson | A61B 3/1025 351/205 |
| 2012/0154747 A1 | 6/2012 | Makihira | |
| 2019/0290124 A1 | 9/2019 | Laforest et al. | |
| 2020/0241136 A1* | 7/2020 | Pang | B60Q 1/1407 |

* cited by examiner

SYSTEMS AND METHODS FOR IMAGING AND CHARACTERIZING OBJECTS INCLUDING THE EYE USING NON-UNIFORM OR SPECKLE ILLUMINATION PATTERNS

CROSS-REFERENCE TO RELATED APPLICATIONS

This application is a national stage of International Patent Application No. PCT/US2020/053656 filed on Sep. 30, 2020; which claims priority to U.S. Provisional Patent Application No. 62/908,151 filed on Sep. 30, 2019, the entire contents of each of which is incorporated by reference herein.

STATEMENT OF FEDERALLY SPONSORED RESEARCH

This invention was made with government support under grant number EY029854 awarded by National Institutes of Health. The government has certain rights in the invention.

TECHNICAL FIELD

Various embodiments of the present technology relate generally to imaging of objects. More specifically, some embodiments of the present technology provide systems and techniques for improved imaging of the ocular fundus, including in vivo imaging.

BACKGROUND

Continuous advances in imaging technologies have led to remarkable developments in a wide variety of fields. For instance, imaging technology improvements have provided a better understanding of disease mechanisms, design of innovative therapies (e.g., microsurgery, laser, etc.), and characterization of markers of disease progression and treatment efficiency. In particular, in the last three decades, the diagnosis and management of ophthalmic diseases has been transformed by the advent of optical coherence tomography (OCT). Despite these remarkable developments in imaging technologies, including OCT and more recently adaptive-optics retinal imaging as well as their combination, many of the retinal structures critical to vision remain difficult to image in vivo. Hence, new methods are warranted to uncover such structures in the living human eye.

Increasingly, progress is much awaited as the percentage of people with blinding and vision disabling conditions continues to grow. This is mainly the result of an increasing aging population and chronic health conditions resulting in an increase in prevalence of age-related macular degeneration (AMD), vascular diseases (e.g., diabetic retinopathy), long-term complications of glaucoma, and others, which, to date, are only partially treatable or preventable.

SUMMARY

Various embodiments of the present technology generally relate to systems and methods for imaging and characterizing objects including the eye using non-uniform or speckle illumination patterns.

In a first aspect of the present technology, a method for characterizing at least a portion of an object is provided. The method may include generating, using at least one light source, one or multiple non-uniform illumination patterns on an object. The method may also include detecting, using a detector, backscattered light from the object in response to the generating. The method may further include extracting, using the detector, data representative of the backscattered light. The method may also include processing, using a processing unit, the data representative of the backscattered light to create one or more images of at least a portion of the object.

In an example of the method according to the first aspect of the present technology, the generating step of the method may include scanning, using the at least one light source, the one or multiple non-uniform illumination patterns over the object.

In another example of the method according to the first aspect of the present technology, the one or multiple non-uniform illumination patterns include at least one speckle pattern. In this example, the processing step of the method may include processing the data representative of the backscattered light using one or more algorithms for blind speckle-structured-illumination.

In any of the above examples of the method according to the first aspect of the present technology, the generating step of the method may include illuminating at least a portion of the object with light of at least two colors. In this example, the illuminating step of the method may include generating at least two different speckle patterns including: a first speckle pattern of a first color of light, and at least a second speckle pattern of at least a second color of light.

In any of the above examples of the method according to the first aspect of the present technology, the processing step of the method may include processing the data to generate: one or more depth images, or optical section, of the at least a portion of the object.

In any of the above examples of the method according to the first aspect of the present technology, the processing step of the method may include processing the data representative of the light backscattering to characterize at least one aberration of the object.

In any of the above examples of the method according to the first aspect of the present technology, the processing step of the method may include determining at least one of: illumination, and at least one aberration, of the object.

In any of the above examples of the method according to the first aspect of the present technology, the processing step of the method may be performed or otherwise implemented (e.g., at least in part using a computing device) using one or more of: an optimization algorithm, a gradient descent algorithm, a convex optimization, a simulated annealing algorithm, a maximum likelihood estimation, a Bayesian estimation, a neural network, and a machine learning optimization.

In any of the above examples of the method according to the first aspect of the present technology, the processing step of the method may be performed or otherwise implemented (e.g., at least in part using a computing device) using at least one of: a regularization process, a Tichonov regularization, a sparsity constraint, a nuclear norm constraint, a mean-constrained, a least absolute shrinkage and selection operator regularization, a total variation regularization, and a basis pursuit.

In any of the above examples of the method according to the first aspect of the present technology, the object may include an ocular structure of an eye.

In a second aspect of the present technology, a method for characterizing at least a portion of an ocular structure of the eye is provided. The method may include sensing an ocular structure of an eye using speckle structured-illumination to generate speckle images of at least a portion of the ocular structure.

In an example of the method according to the second aspect of the present technology, the method may include characterizing an eye aberration based on the speckle images.

In another example of the method according to the second aspect of the present technology, at least one of: the sensing step, and the characterizing step, may include processing (e.g., at least in part using a computing device) data representative of detected light emanating from the eye as a result of one or more of: scattering, reflection, absorption, fluorescence, two-photon excitation, and high harmonic generation.

In any of the above examples of the method according to the second aspect of the present technology, the processing step may include processing (e.g., at least in part using a computing device) the data using one or more algorithms for blind speckle-structured-illumination.

In any of the above examples of the method according to the second aspect of the present technology, the sensing step may include imaging the ocular structure.

In a third aspect of the present technology, a system for characterizing at least a portion of an object is provided. The system may include at least one light source to generate one or multiple non-uniform illumination patterns on an object. The system may also include a detector array to extract data representing backscattering from the object. The system may further include a processing unit. The processing unit may be configured to receive the data representing backscattering from the object. The processing unit may also be configured to generate one or more images of at least a portion of the object.

In an example of the system according to the third aspect of the present technology, the at least one light source may be configured to scan the one or multiple non-uniform illumination patterns over the object.

In another example of the system according to the third aspect of the present technology, the one or multiple non-uniform illumination patterns may include at least one speckle pattern.

In any of the above examples of the system according to the third aspect of the present technology, the processing unit may be further configured to process the data representing backscattering from the object using one or more algorithms for blind speckle-structured-illumination.

In any of the above examples of the system according to the third aspect of the present technology, the at least one light source may include a laser.

In any of the above examples of the system according to the third aspect of the present technology, the at least one light source may be configured to illuminate at least a portion of the object with light of at least two colors. In this example, the at least one light source may be further configured to illuminate the at least a portion of the object with at least two different speckle patterns including: a first speckle pattern of a first color of light, and at least a second speckle pattern of at least a second color of light.

In any of the above examples of the system according to the third aspect of the present technology, the processing unit may be further configured to process the data representing backscattering from the object to generate: one or more depth images, or optical sections, of the at least a portion of the object.

In any of the above examples of the system according to the third aspect of the present technology, the processing unit may be further configured to process the data representing backscattering from the object to characterize at least one aberration of the object.

In any of the above examples of the system according to the third aspect of the present technology, the processing unit may be further configured to process the data representing backscattering from the object to determine at least one of: illumination, and at least one aberration, of the object.

In any of the above examples of the system according to the third aspect of the present technology, the processing unit may be further configured to process the data representing backscattering from the object using one or more of: an optimization algorithm, a gradient descent algorithm, a convex optimization, a simulated annealing algorithm, a maximum likelihood estimation, a Bayesian estimation, a neural network, and a machine learning optimization.

In any of the above examples of the system according to the third aspect of the present technology, the processing unit may be further configured to process the data representing backscattering from the object using at least one of: a regularization process, a Tichonov regularization, a sparsity constraint, a nuclear norm constraint, a mean-constrained, a least absolute shrinkage and selection operator regularization, a total variation regularization, and a basis pursuit.

In any of the above examples of the system according to the third aspect of the present technology, the object is an ocular structure of an eye.

In a fourth aspect of the present technology, a method for characterizing at least a portion of an eye is provided. The method may include illuminating an eye using one or multiple speckle structured-illumination patterns. The method may also include detecting light backscattered by an ocular fundus of the eye in response to the illuminating.

In an example of the method according to the fourth aspect of the present technology, the method may include creating (e.g., at least in part using a computing device) one image or a series of images using the light backscattered by the ocular fundus.

In another example of the method according to the fourth aspect of the present technology, the method may include mapping (e.g., at least in part using a computing device) each pixel of the image or series of images to an area on the ocular fundus.

In any of the above examples of the method according to the fourth aspect of the present technology, one or both of the illuminating step and the detecting step may be performed or otherwise implemented trans-pupillary or trans-scleral.

In any of the above examples of the method according to the fourth aspect of the present technology, the illuminating step may include directing laser light through a scattering medium to generate a speckle pattern on the ocular fundus.

In any of the above examples of the method according to the fourth aspect of the present technology, the detecting step may include scanning the speckle pattern over at least a portion of the ocular fundus. In this example, the method may include modifying the speckle pattern over time. In this example, one or both of: the illuminating step, and the detecting step, may include processing (e.g., at least in part using a computing device) data representative of the light backscattering using one or more algorithms for blind speckle-structured-illumination.

In any of the above examples of the method according to the fourth aspect of the present technology, the detecting step may include detecting at least one of: light that is reflected from the ocular fundus; and light resulting from fluorescence from intrinsic or extrinsic substances in or on the ocular fundus.

In any of the above examples of the method according to the fourth aspect of the present technology, the detecting step may include detecting light emanating from the eye as a result of one or more of: scattering, reflection, absorption, fluorescence, two-photon excitation, and high harmonic generation.

In any of the above examples of the method according to the fourth aspect of the present technology, the method may include processing (e.g., at least in part using a computing device) data representative of the light backscattering to characterize at least one aberration of the eye.

In any of the above examples of the method according to the fourth aspect of the present technology, the method may include processing (e.g., at least in part using a computing device) data representative of the light backscattering to determine at least one of: illumination, and at least one aberration, of the object.

In any of the above examples of the method according to the fourth aspect of the present technology, the method may include processing (e.g., at least in part using a computing device) data representative of the light backscattering using one or more of: an optimization algorithm, a gradient descent algorithm, a convex optimization, a simulated annealing algorithm, a maximum likelihood estimation, a Bayesian estimation, a neural network, and a machine learning optimization.

In any of the above examples of the method according to the fourth aspect of the present technology, the method may include processing (e.g., at least in part using a computing device) data representative of the light backscattering using at least one of: a regularization process, a Tichonov regularization, a sparsity constraint, a nuclear norm constraint, a mean-constrained, a least absolute shrinkage and selection operator regularization, a total variation regularization, and a basis pursuit.

In any of the above examples of the method according to the fourth aspect of the present technology, the creating step may include processing (e.g., at least in part using a computing device) the one image or the series of images to generate at least one super-resolution image of at least a portion of the oculus fundus.

In any of the above examples of the method according to the fourth aspect of the present technology, the method may include processing (e.g., at least in part using a computing device) data representative of the light backscattered by the ocular fundus to generate: one or more depth images, or optical sections, of at least a portion of the oculus fundus.

In a fifth aspect of the present technology, a system is provided. The system may include a laser to generate one or multiple non-uniform illumination patterns on an ocular fundus of an eye. The system may also include a detector array to extract data representing backscattering from the ocular fundus. The system may further include a processing unit. The processing unit may be configured to receive the data representing backscattering from the ocular fundus. The system may also be configured to generate one or more images of the ocular fundus.

In an example of the system according to the fifth aspect of the present technology, the processing unit may be further configured to process the data representing backscattering from the ocular fundus to generate: one or more depth images, or optical sections, of at least a portion of the oculus fundus.

In a sixth aspect of the present technology, an eye imaging system is provided. The eye imaging system may include a light source for illumination. The eye imaging system may also include a detector array to collect backscattered, or fluorescence, light from an eye or an ocular structure. The eye imaging system may further include a mask to isolate an illumination path and a detection path. The eye imaging system may also include a processing unit. The processing unit may be configured to receive data representing the backscattering, or fluorescent, light. The processing unit may also be configured to generate one or more images of the ocular structure.

In an example of the eye imaging system according to the sixth aspect of the present technology, the mask may be, or may include, a binary mask. In this example, the binary mask may be, or may include, a spoke-wheel mask.

In another example of the eye imaging system according to the sixth aspect of the present technology, the mask may be configured to isolate the illumination path and the detection path. In this example, the isolation of the illumination path and the detection path by the mask may facilitate maximizing a numerical aperture.

BRIEF DESCRIPTION OF THE DRAWINGS

Embodiments of the present technology will be described and explained through the use of the accompanying drawings.

The drawings have not necessarily been drawn to scale. Similarly, some components and/or operations may be separated into different blocks or combined into a single block for the purposes of discussion of some of the embodiments of the present technology. Moreover, while the technology is amenable to various modifications and alternative forms, specific embodiments have been shown by way of example in the drawings and are described in detail below. The intention, however, is not to limit the technology to the particular embodiments described. On the contrary, the technology is intended to cover all modifications, equivalents, and alternatives falling within the scope of the technology as defined by the appended claims.

DETAILED DESCRIPTION

Various embodiments of the present technology relate generally to imaging. More specifically, some embodiments of the present technology provide systems and techniques for improved in vivo imaging of the ocular fundus. Various embodiments of the present technology could enable better understanding of the pathogenesis and progression of retinal diseases, including some of the most severe vision disabling conditions (e.g., retinal dystrophies, AMD, glaucoma), but also enable earlier diagnosis, as well as spur and accelerate the development of innovative therapeutic strategies aiming to protect cellular and sub-cellular structures before irreversible cell death and blindness occur. For example, new therapeutic strategies, such as retinal prostheses, gene therapy (corrective, neuroprotective, and more recently optogenetics) are entering preclinical validation studies and clinical trials, with initial results that are promising, giving hope for vision preservation and even restoration in several conditions.

The high resolution targeted by the described techniques could facilitate the validation of, and patient selection for, such emerging therapies, while enabling the discovery and characterization of novel biomarkers, quantifiable clinical outcome measures, and clinical endpoints. While modifying and improving the diagnosis and treatment of retinal diseases, the methods and systems presented here have the potential to significantly impact current clinical practice. Furthermore, because the retina is the most optically and functionally approachable part of the brain the significance of this technology extends into the field of neuroscience.

In the following description, for the purposes of explanation, numerous specific details are set forth in order to provide a thorough understanding of embodiments of the present technology. It will be apparent, however, to one skilled in the art that embodiments of the present technology may be practiced without some of these specific details.

The techniques described here can be embodied as special-purpose hardware (e.g., circuitry), as programmable circuitry appropriately programmed with software and/or firmware, or as a combination of special-purpose and programmable circuitry. Hence, embodiments may include a machine-readable medium having stored thereon instructions which may be used to program a computer (or other electronic devices) to perform a process. The machine-readable medium may include, but is not limited to, floppy diskettes, optical disks, compact disc read-only memories (CD-ROMs), magneto-optical disks, ROMs, random access memories (RAMs), erasable programmable read-only memories (EPROMs), electrically erasable programmable read-only memories (EEPROMs), magnetic or optical cards, flash memory, or other type of media/machine-readable medium suitable for storing electronic instructions.

The phrases "in some embodiments," "according to some embodiments," "in the embodiments shown," "in other embodiments," and the like generally mean the particular feature, structure, or characteristic following the phrase is included in at least one implementation of the present technology, and may be included in more than one implementation. In addition, such phrases do not necessarily refer to the same embodiments or different embodiments.

Figure 1A:
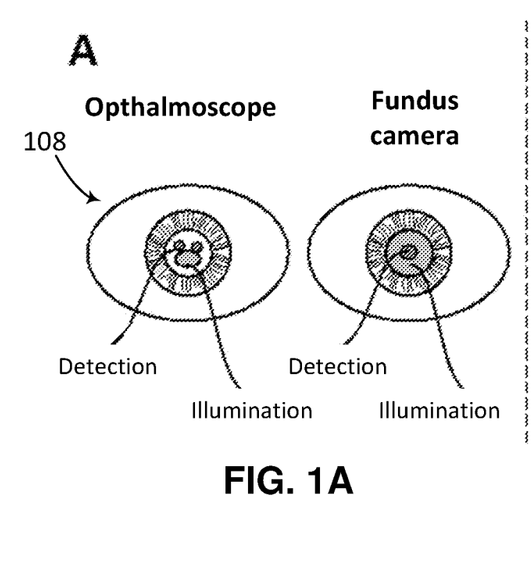
FIG. 1A illustrates that in a conventional ophthalmoscope or fundus camera, the illumination uses most of the pupillary area with a separate small area reserved for observation.

A key shortcoming shared by existing optical approaches for retinal imaging is that the attainable size of the eye's pupil sets a limit on the numerical aperture, and hence the lateral resolution. In many instruments, illumination and detection pathways have to be shared, but be separated within, this sole aperture of the eye 108 (FIGS. 1A-1B), further constraining the achievable resolution. Note that such separation is needed as the cornea reflects about 2% of the incident light, whereas the observed retinal image is only 0.1%. Systems can also include polarization devices to separate incident and reflected light, such as polarizers, polarizing beam splitters, or optical isolation using circular polarization.

Various embodiments of the present technology address these shortcomings, making use of understanding in the field of light propagation in complex media and of super-resolution imaging. Some embodiments offer an imaging approach that can provide detail of the ocular fundus beyond what is possible by state-of-the-art imaging modalities. For example, recent advances in concepts of light control in random media, giving rise to complex illumination patterns—e.g., speckle—have led to remarkable developments for imaging through or in scattering media 126. In parallel, emerging approaches in structured illumination (e.g., blind structured-illumination microscopy, a deconvolution-based approach not requiring any a priori knowledge of the illumination patterns 101) using speckle have demonstrated super-resolution imaging capability.

Figure 1B:
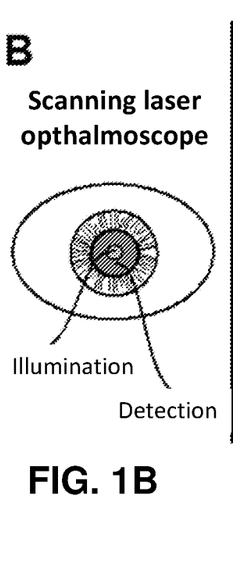
FIG. 1B illustrates that in a scanning laser ophthalmoscope, inversion of the illumination and detection pathways is enabled, using the larger pupillary area for observation and the smaller one for illumination.
Figure 1C:
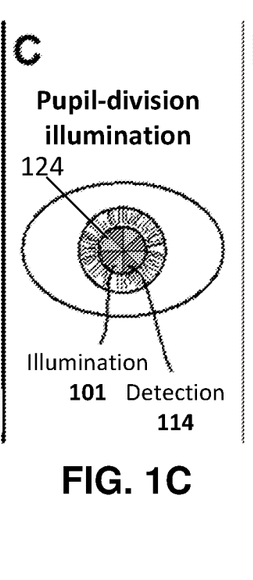
FIG. 1C illustrates an example of a trans-pupillary approach which enables doubling the classical resolution by use of speckle illumination and a spoke-wheel mask to isolate the illumination and detection paths with maximal aperture.
Figure 1D:
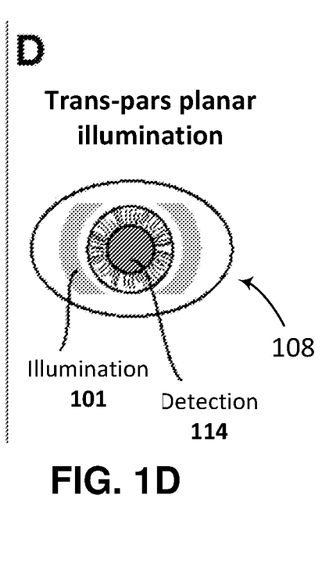
FIG. 1D shows that by illuminating through the sclera (pars plana), the entire pupillary area can be used for observation of the ocular fundus and the illumination and detection numerical-aperture (NA) maximized.

Unlike the conventional ophthalmoscope or fundus camera, where illumination uses most of the pupillary 152 area with a separate small area reserved for observation (see, e.g., FIG. 1A), the scanning laser ophthalmoscope for the first time allowed inversion of the illumination 120 and detection 122 pathways, using the larger pupillary 152 area for observation and the smaller one for illumination (see, e.g., FIG. 1B). FIG. 1C illustrates a trans-pupillary 152 approach that enables doubling the classical resolution by use of speckle illumination 101 and possibly a mask 123, such as a spoke-wheel mask 124, to isolate the illumination 120 and detection 122 paths, preserving a maximal aperture. In another example, a binary mask other than the spoke wheel mask 124 may be used in system 100 for a same or similar purpose. In addition, FIG. 1D shows that by illuminating through the sclera 154 (pars plana), the entire pupillary 152 area can be used to provide an observation area 107 of the ocular fundus 106 and the illumination numerical-aperture (NA) maximized.

Various embodiments of the methods (e.g., method 1000) and systems (e.g., system 100) here disclosed expand these techniques for the use in ophthalmology, and in particular describe speckle structured-illumination of the ocular fundus 106 with high-resolution image 105 reconstruction (e.g., a few micron to sub-micron resolution). In other words, by illuminating the ocular fundus 106 using speckle patterns 103, either through the pupil 152 or the sclera 154, various embodiments of the present technology can boost the resolution and reveal otherwise inaccessible details of the retina. Note that, similar to confocal microscopy, resolution is determined by the illumination as well as the detection point spread function (PSF). While the spot size of a focused beam on the retina is degraded by aberrations 132 requiring correction via adaptive optics, the size of speckle patterns 103 is not; therefore, enabling improvements in resolution. Various embodiments of the present technology provide for a novel aberration 132 insensitive image 105 reconstruction approach that takes advantage of speckle illumination, "wide field" image 105 detection and computational reconstruction. Because data acquisition is based on fast camera image 105 frames, eye-motion artifacts are minimized after precise registration of the images 105 acquired.

Specifically, some embodiments can incorporate a speckle illumination scheme to overcome the NA limitations inherent to current systems. The concept can be implemented trans-pupillary 152 or trans-scleral 154 (more precisely through the pars plana, which lacks muscle, blood vessels, or pigmentation) allowing the entire pupil 152 to be used for backscattered light 114 collection, while simultaneously increasing the illumination NA (FIG. 1D).

In trans-pupillary 152 illumination implementation, a light source 122 (e.g., laser 102) directed through a scattering diffuser (e.g., "D/A") generates a speckle pattern 103 (speckle structured-illumination) on the ocular fundus 106 that is scanned or modified over time. A fast camera provides images 105 that are precisely registered. Reconstruction algorithms provide high- (or super-) resolution images 105 of the ocular fundus 106 that can improve the resolution currently achieved via adaptive optics. As a by-product, the aberrated PSF of the eye 108 is also recovered.

In trans-pars-planar 154 illumination, the light (forward) scattered by the sclera 154 generates a speckle pattern 103 on the ocular fundus 106 that can be similarly scanned utilizing the so-called shift memory effect. The backscattered light 114 is then collected through the entire pupil 152, imaged, and processed to recover high resolution retinal images 105.

Diffraction-limited systems classically present a resolution restricted by the numerical aperture (NA) and the detection wavelength ($\lambda$), $\delta x \sim 0.61 \lambda / NA$. Computational imaging using multiple illumination patterns 101 has shown potential to overcome these limitations. The key principle is to use multiple non-uniform illumination patterns 104 shining the sample and extract data 112 with a detector array 110. The spatial frequency mixing of the object (fluorescence/absorption/scattering) function with the illumination pattern 101 results in a down-shifting modulation of the sample's high spatial frequencies into the frequency bandpass of the system 100. Data 112 post-processing by a processing unit 116 (e.g., a general, or special, purpose computer) provides increased resolution up to a factor of ×2 in the linear regime or even higher. Unfortunately, most prior techniques require well-defined sinusoidal or other deterministic patterns that require precise control to avoid aberrations 132 and distortions. Implementation of this constraint in retinal imaging is challenging if not impossible due to the inherent aberrations 132 introduced by the eye 108 as well as the inherent and involuntary physiological movements of the eye 108.

Recent work in the field of structured illumination fluorescence microscopy has, however, shown that image 105 reconstruction can be performed without knowledge of the illumination patterns 101. Various embodiments of the present technology extend this approach to the imaging of the eye 108 using coherent light scattering and further explore the use of illumination through the sclera 154, more precisely the pars plana 154. The key observation is that this blind structured-illumination method increases the effective NA and is insensitive to aberrations 132 via computational correction while not requiring any calibration step, making it attractive for ocular fundus 106 imaging.

Reconstruction from Unknown Speckle Illumination Patterns

An alternative appealing approach to sinusoidal pattern illumination is to use stochastic (speckle) illumination with known or unknown patterns 101. The former is inappropriate for imaging of the ocular fundus 106 because one cannot calibrate the projected patterns 101 due to eye 108 aberrations 132. However, the latter is particularly attractive for retinal imaging because there is no need to measure the illumination patterns 101. The concept has been demonstrated in optical fluorescence microscopy, using incoherent sources and photoacoustic imaging. Algorithms for blind speckle-structured-illumination (BSSI) are able to estimate the sample fluorescence from low-resolution images obtained under unknown excitation patterns. As applied to the embodiments of systems and methods according present technology described herein, "blind" in BSSI means the speckle pattern used in the illumination is unknown or only partially known. Further, when a single speckle pattern is scanned, the estimation algorithms provide a reconstruction by simultaneously estimating the scanning shifts, the speckle illumination, and the object under observation. An important feature is that speckle patterns 103 preserve their statistical characteristics when propagating through a system with aberrations 132 like the eye 108. Various embodiments include algorithms capable to perform this functionality including BSSI with coherent backscattering from the object, making them suitable for retinal imaging and the visualization of cells beyond those that contain endogenous fluorophores (e.g., in the retinal pigment epithelium that may be visualized by means of autofluorescence imaging) and without the administration of fluorescent dyes (e.g., in fluorescein or indocyanine green angiography).

As an example algorithm of blind deconvolution, one can recover the object, the point spread function (PSF) of the aberrations, the shift of the speckle patterns, and the illumination speckle impinging on the object from a set of images of the speckle-illuminated object corresponding to different shifts. The algorithm requires the acquisition of a number N of images of the object for each position where the phase of the light field is recovered using phase-shifting interferometry. Once the N images are obtained including amplitude and phase, an optimization algorithm is used to reconstruct the object. For instance, such group of algorithms includes a gradient descent algorithm, convex optimization, simulated annealing, maximum likelihood, Bayesian estimation, a neural network or machine learning optimization. These algorithms can also include some type of regularization, such as Tichonov, sparsity, nuclear norm, mean-constrained, lasso (least absolute shrinkage and selection operator), total variation, basis pursuit, or other types of regularizers.

The image model can be considered as a convolution of a PSF and the object, $y=h\otimes(\rho I)$, where y is the complex amplitude image collected by the camera and phase shifting interferometry, h is the PSF of the aberration, ρ is the object and I.

A stochastic gradient descent algorithm with a convex block criterion can be used to solve the minimization problem. Namely one seeks to find estimates for ρ, h, I, as well as the shift positions.

The minimization seeks to minimize J, defined as follows:

$$J = \sum_i \|y^i - h^k \otimes (\rho^k I_i^k)\|^2$$

where i is an index on the illumination pattern, and k indicates the iteration number. The gradient descent is applied with respect to the h, ρ, and I: $\nabla_h J$, $\nabla_\rho J$, $\nabla_I J$, such that each iteration of a least square minimization with a block convex criterion includes the following steps:

An update of the object following the gradient descent:
$\nabla_\rho J = \nabla_\rho \Sigma_i \|y^i - h^k \otimes (\rho^k \cdot I_i^k)\|^2$ An update of the object following the gradient descent:
$\nabla_I J = \nabla_I \Sigma_i \|y^i - h^k \otimes (\rho^k \cdot I_i^k)\|^2$ An update the PSF following the gradient descent:
$\nabla_h J = \nabla_h \Sigma_i \|y^i - h^k \otimes (\rho^k \cdot I_i^k)\|^2$ In different embodiments, the various speckle patterns 103 can, for example, be generated at random, pre-selected from a given (e.g., predetermined) set of patterns 103, obtained by inverse design, or alternatively be the result of scanning a given speckle pattern 103, either in a raster scanning fashion or at random.

Figure 2:
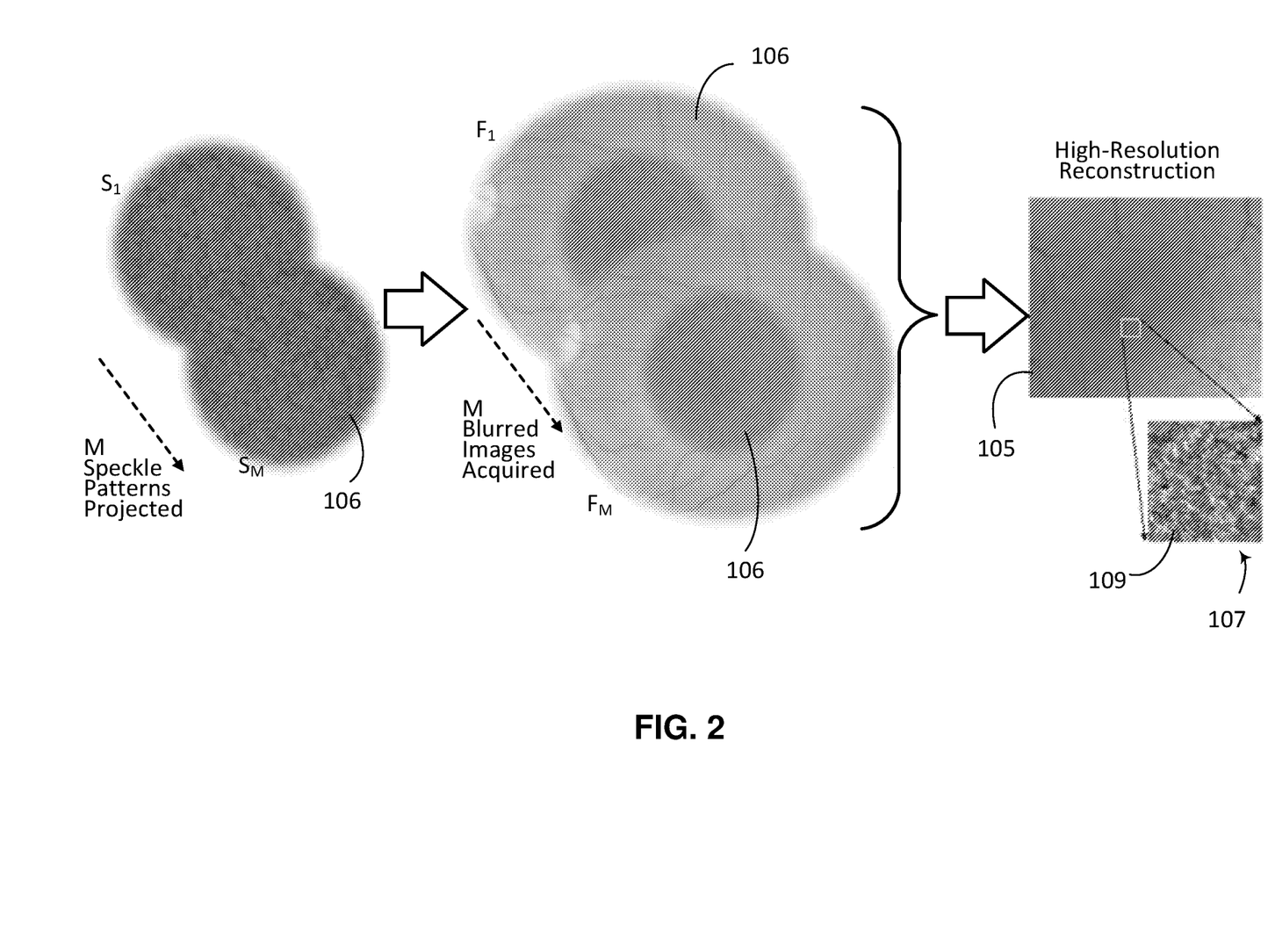
FIG. 2 illustrates a sequence of shifted speckle patterns that are projected onto the retina and imaged through the eye's pupil from which various computational techniques are used to reconstruct the image with improved resolution (up to double the resolution traditionally dictated by the NA of the pupil and the detection wavelength, and possibly beyond that).

Note that structured illumination imaging generates super-resolved images 105 corresponding to an effective PSF, $h_{eff}=|h_1 h_2|^2$, where $h_1$ is the illumination system PSF and $h_2$ is the collection system PSF. Further improvements in resolution can be achieved via advanced regularization in the inversion scheme, such as sparsity priors. In some embodiments, speckle illumination is shined onto the retina, light is back-scattered from the ocular fundus 106 and propagates through the pupil 152 to the imaging system 100. The method can be based on acquiring M images 105, $F_1, \ldots, F_M$ (N×N pixels 109), of the sample illuminated under M (random) speckle patterns 103 that differ in a lateral shift (FIG. 2). The acquired images 105 are modeled as a convolution between a PSF and the product of the object and the illumination pattern 101. The system model considered is $$F_m(r) = \int h_2(r-r')\rho(r')S_m(r')dr' + \varepsilon_m(r), m=1\ldots M \quad (1)$$

where ρ(r) is the sample (fluorescence, absorption, scattering) function defining the contrast mechanism, $S_m$ is the m-th speckle pattern 103 and $\varepsilon_m$ is the noise (here considered additive for simplicity). The PSF ($h_2$) is the combined optical response of the eye 108 and instrument optics. This general formalism includes the case of coherent backscattering from the ocular fundus 106.

Some embodiments can determine the object (e.g., retina or choroid) from the M low-resolution images 105. Because the system 100 is highly underdetermined further assumptions are made, such as that the illumination intensities are homogeneous on average. Additional regularization constraints can be used to match the physical process and improve the reconstruction, including positivity or sparsity constraints.

The object can be estimated by minimizing a cost functional iteratively, for example via conjugate gradient algorithms. Some embodiments can recover simultaneously the three unknowns: PSF (h), illumination (I), and object ρ.

$$J = \Sigma_{k=1}^N \|h \otimes (\rho \cdot I^{(k)}) - y^{(k)}\|^2 \quad (2)$$

where $y^{(k)}$ is the $k^{th}$ recorded image 105 and $I^{(k)}$ is the illumination shifted to the $k^{th}$ position. The result is a simultaneous estimation of the object (retina) and (eye) aberrations 132.

Optimal Algorithms for Reconstruction Under Coherent Light Scattering (Non-Fluorescence)

Some traditional methods developed for fluorescence microscopy are applicable to the imaging of the ocular fundus 106. For instance, using autofluorescence imaging of endogenous fluorophores of the retina or fluorescence imaging after administering fluorescent dyes.

Alternatively (when not in fluorescence mode), while constraints such as non-negativity are applied to fluorescence images 105, they are not valid for coherent backscattered imaging, where particular attention is needed to deal with the phase of the complex amplitude of the field. In order to solve the coherent BSSI case, some embodiments use regularization conditions (see, e.g., FIGS. 3A-3B). Further, some embodiments approach the coherent BSSI as a generalization of ptychography, with particular attention given to the avoidance of artifacts through redundancy. Strict tests can be run to compare reconstructions with ground truth. A critical characteristic of coherent methods is its ability to accurately reconstruct the phase information that helps uncover weakly absorbing structures. Solving the speckle illumination inverse problem under a coherent scattering framework is a useful innovation.

Figure 3A:
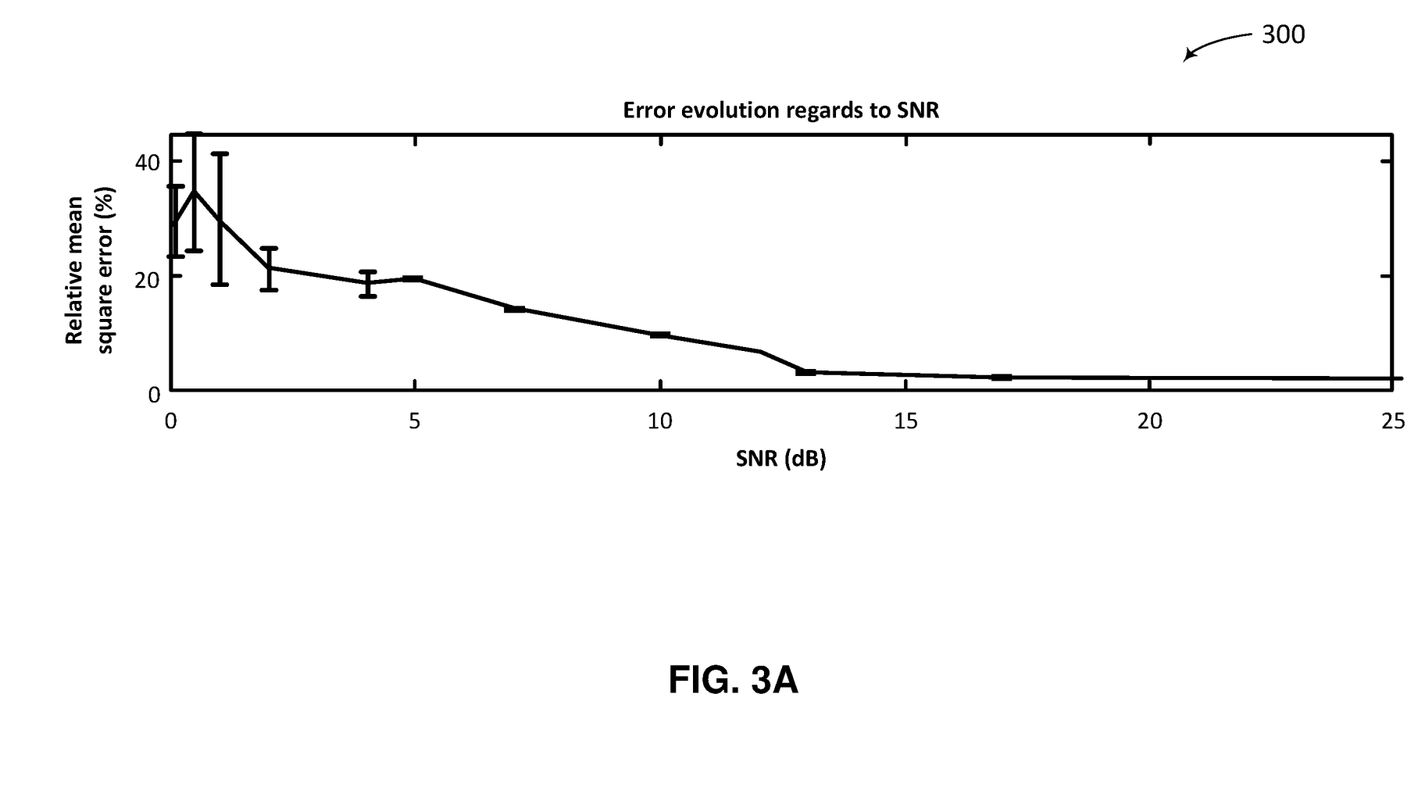
FIG. 3A is a plot showing the relative mean square error (RMSE) as a function of the signal-to-noise ratio (SNR) that may be present in some embodiments of the present technology after the reconstruction process.
Figure 3B:
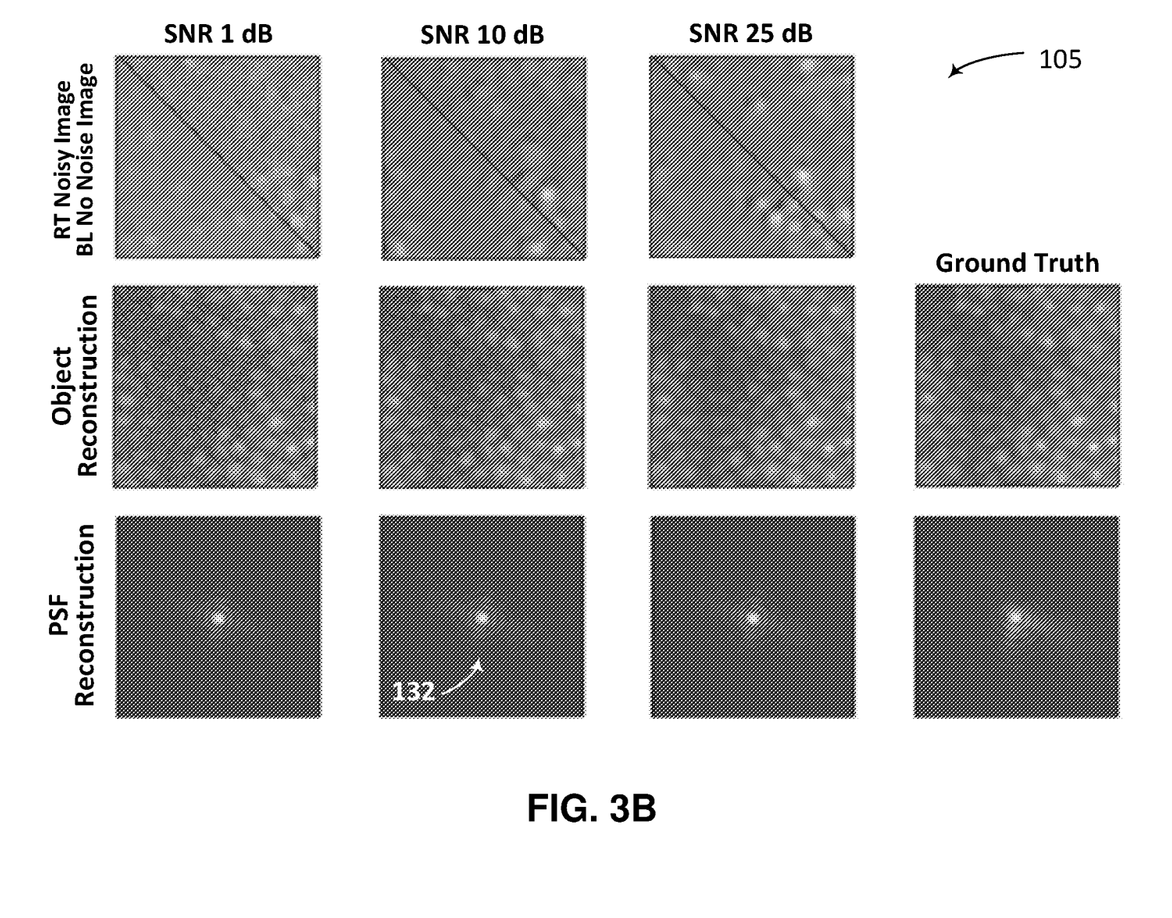
FIG. 3B illustrates reconstructions of simulated images showing the capability of one of the various embodiments of the present technology to recover high resolution images as well as the PSF from highly noisy and blurred data with a ground truth of a high-resolution image of the photoreceptor cone mosaic (BL=bottom left, RT=right top).

FIGS. 3A-3B presents reconstructions of simulated images 105 showing the capability of the method to recover high resolution images 105 as well as the PSF from highly noisy and blurred data. FIG. 3A is a plot 300 showing the relative mean square error (RMSE) as a function of the signal-to-noise ratio (SNR). The ground truth is a high-resolution image 105 of the photoreceptor cone mosaic. Zernike coefficients measured using an aberrometer are used to simulate a realistic human eye 108 PSF. A fully developed speckle is used as illumination. Images 105 are simulated by shifting the speckle illumination, multiplying it by the object and performing a convolution with the PSF.

Gaussian additive noise is added with variance calculated to give the desired SNR. A total of 15*15=225 images 105 are simulated by shifting the illumination in x and y directions. A reconstruction of the retinal image 105 and of the ocular aberrations 132 (PSF) is performed by minimizing a fidelity to data term (Eq. 2). FIG. 3B illustrates reconstructions of simulated images 105 showing the capability of the various embodiments of the present technology to recover high resolution images 105 as well as the PSF from highly noisy and blurred data with a ground truth of a high-resolution image 105 of the photoreceptor cone mosaic.

Effect of Ocular Aberrations

In some embodiments, the illumination can be a speckle pattern 103 generated either by the scattering of the sclera 154 (trans-pars-planar illumination) or a diffuser (trans-pupillary 152 illumination). The phase randomness of the speckle can cancel the effects of the aberrations 132 in the illumination path 120 (the statistical randomness of the speckle is not altered by the aberrations 132). As a result, some embodiments can use the speckle pattern 103 for measuring the aberrations 132 of the imaging path 122. The estimation of the eye's 108 aberrations 132 via the speckle pattern 103 illumination is also a novel aspect of this technology. The general principle was demonstrated in fluorescence ex vivo experiments via maximum likelihood deconvolution. With BSSI, some embodiments can now calculate the aberrated PSF without calibration, even for spatially-varying aberrations.

A wavefront sensor is not required in various embodiments, nor the generation of an artificial guide star. This significantly simplifies the setup with respect to conventional adaptive optics implemented with a deformable mirror or computational adaptive optics. BSSI acquisition enables several advantages as compared to deformable mirror approaches and existing computational correction methods. Notably, the absence of specific adaptive optics hardware makes for a simpler and more compact system 100.

Figure 4:
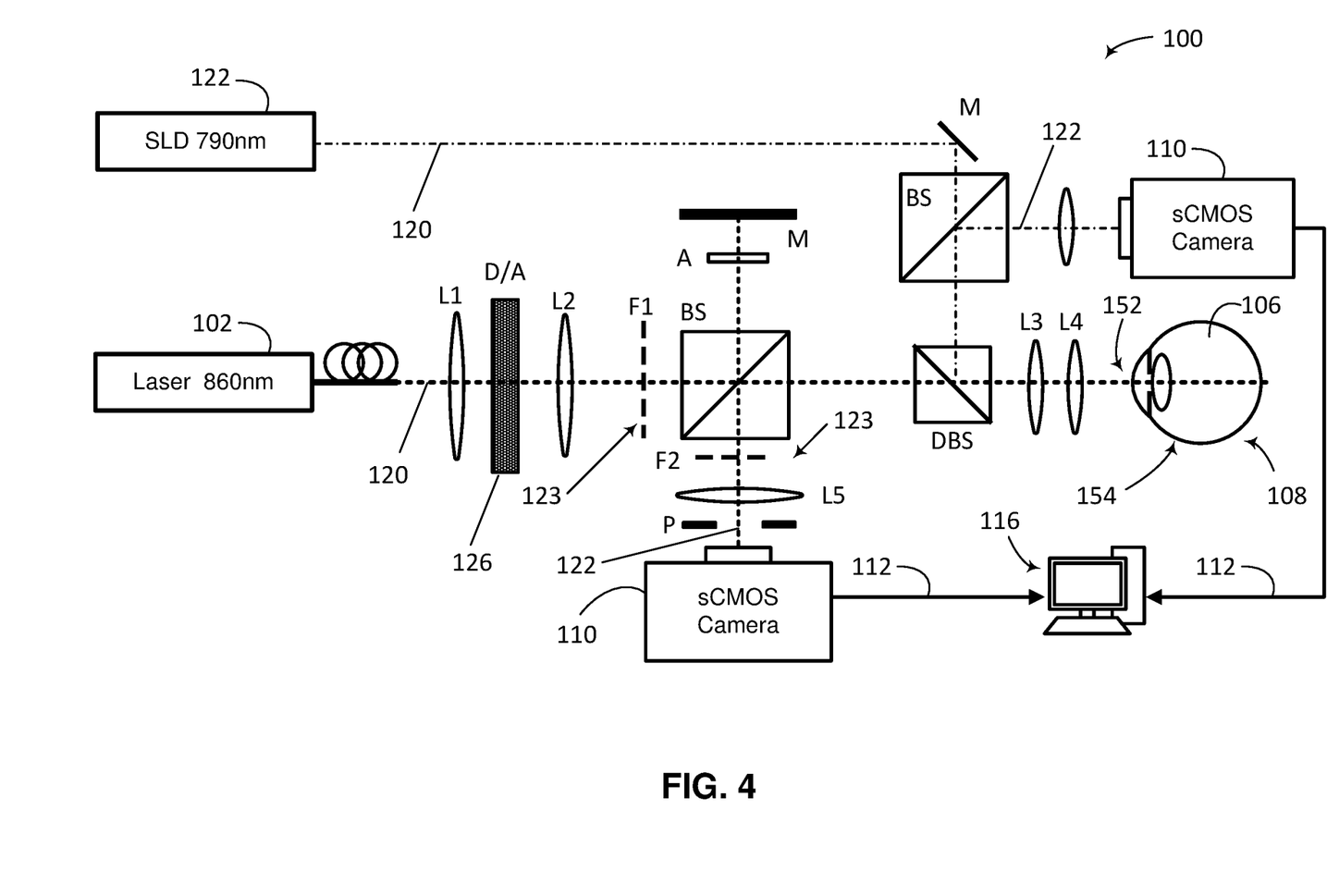
FIG. 4 is a block diagram illustrating an example of experimental setup that may be used in some embodiments of the present technology. SLD=super-luminescent diode; L1, L2, L3, L4, L5 represent lenses; BS=beam splitter; DBS=dichroic beam splitter; F1 and F2 are masks to separate illumination and detection light; A is an axicon to generate ring illumination; P is a pupil; D/A is a diffuser.

A scheme of the optical setup of system 100 according to an embodiment of the present technology is depicted in FIG. 4. Among the possible operational implementations are: trans-pupillary 152 and trans-pars-planar 154 illumination.

Implementation of Trans-Pupillary and Trans-Pars-Planar Speckle Structured-Illumination In both cases, laser 102 light is delivered via a fiber and collimated with a lens (L1). In trans-pupillary 152 illumination, a diffuser (D) will generate the speckle patterns 103 projected onto the retina, while an optional mask 123 (e.g. spoke wheel 124, F1, F2) conjugated to the pupil 152 or cornea may be used, separating illumination and detection to avoid reflections while preserving the maximum NA along both paths 120 and 122. If needed, an engineered (e.g., computer generated) diffuser using diffractive optics to attain better control (e.g. uniformity) of the speckle patterns 103 can be used.

The sclera 154 forms an external fibrous covering of the eye 108 beyond the cornea, containing thick and densely packed collagen fibrils that makes it strongly light scattering. Scattering and absorption through the sclera 154 is reduced at longer wavelengths enabling the use of the so-called memory effect, namely the speckle patterns 103 are preserved upon shifts or tilts of the light with respect to the medium 126. Note that above 800 nm, the scattering coefficient is reduced to <20 cm$^{-1}$, generating a narrow angular distribution of the transmitted light. The pars plana 154, in particular, is a ~4 mm wide band located 3 to 4 mm away from the limbus that lacks muscle, blood vessels, and pigmentation, and thus is ideally suited for trans-scleral 154 illumination. It has previously been utilized to demonstrate contact and non-contact wide-field-of-view imaging. In trans-pars-planar 154 illumination, light passes through an axicon (A) to generate a ring illumination and projected (L2) onto a mask 123 (F1') to generate two arches following the shape of the pars plana 154 without physical contact with the sclera 154 as shown in FIG. 1.

System Design Considerations for Exemplary Embodiment

For speckle illumination, a laser 102 at 860 nm may be used, which provides high transmission and enables high SNR, in both trans-pupillary 152 and trans-pars-planar 154 configurations. The system 100 images the light backscattered 114 by the ocular fundus 106 toward a high-sensitivity scientific CMOS camera or equivalent, e.g. ORCA flash 4-V2 (Hamamatsu), enabling for instance 2048×1024 pixel 109 frame acquisition at 200 Hz.

The laser 102 power may be optimized, and incoherent source power, where, if the latter is used, power source(s) is/are kept within all applicable limits for maximum permissible exposure from the combined system; that is, less than the power stipulated by the ocular safety limits established by the ISO and/or ANSI standards, but sufficient to achieve the target SNR per image 105 frame.

Backscattered laser 102 light 114 from the ocular fundus 106 and exiting through the pupil 152 and cornea bounces from a beam splitter (BS), is collected with a lens system (L3-5) and imaged onto a sCMOS camera directly imaging the retina plane. An optional aperture P further stops unwanted back reflections. An optional arm off the beam splitter provides an interferometric reference. An eye 108 movement tracking and registration system may be employed and use a super-luminescent diode (SLD) at 790 nm along a channel isolated with a dichroic BS (DBS). A wider portion of the retina may be imaged at this wavelength on a second sCMOS camera.

The two sCMOS cameras are synchronized, operating at high rate such as 200 Hz or higher, and controlled by a computer. Post-processing, including image 105 registration and reconstruction are performed in a computer (e.g., processing unit 116) using parallel processing. A fixation target (not shown) is included for in vivo experiments.

Note that despite being a wide-field illumination system 100, the speckle patterns 103 in conjunction with the camera pixels 109 provide inherent sectioning capability in a process similar to a confocal system. This can be explained considering each speckle as a focal spot associated with a virtual pinhole represented by a conjugate pixel 109. The approach resembles recent implementation of parallel Image Scanning Microscopy using multiple illumination spots and engineered PSF. As a result, despite possible crosstalk among channels, the system 100 provides a level of rejection of multiply scattered light from the retina and choroid not present in traditional flood illumination systems.

Multi-Wave Speckle Illumination

When illuminating through a scattering medium 126 (such as the sclera 154) with a continuous wave (CW) laser 102, a monochromatic speckle can be obtained, which has well defined statistical properties (average speckle grain size, intensity distribution, polarization, etc.) useful for image 105 reconstruction. However, a thick scattering medium 126 generates a wavelength-dependent speckle, due to the fact that the path distribution through a volumetric scattering medium 126 can be large (it scales with $L^2/D$ where L is the thickness and D is the diffusivity for the light transport), hence the scattering becomes highly dispersive. Depending on the thickness and scattering properties of the biological layer traversed, the speckle can completely change with wavelength over a fraction of nm to a few nm.

In a generalized implementation, it is possible to use broadband sources 122 (such as superluminescent LED or femtosecond lasers 102) and swept (fastly tunable) sources 122 to obtain a variety of speckle patterns 103 on the retina. As demonstrated in the field of multiple scattering imaging, exploiting such broadband scattered light provides a path towards extracting and/or controlling spectral and temporal aspects of the illumination. In reflection mode, specifically, it enables time-gating and depth-resolved information. These results, obtained in and through highly scattering media 126, bear many similarities with OCT, which achieves depth-resolution by separation of the ballistic from the multiply-scattered light.

Broadband swept-spectrum speckle illumination can achieve depth-resolution and enable 3D reconstruction, a highly-sought property for ophthalmic imaging. Specifically:

Multiple speckle illumination via spectral scanning: even if not seeking any depth resolution, using multiple speckle illumination via spectral tuning of the illumination is an interesting alternative to varying the spatial illumination pattern 101 (or in combination with the latter). Multispectral speckle illumination can be implemented as a way to retrieve additional information towards super-resolution, namely higher resolution than typically allowed by the diffraction limit. This approach is useful, for instance, when the system under investigation has a spectrally varying response (e.g., in fluorescence).

Depth sectioning imaging by multispectral speckle illumination coherence gating: The use of multiple speckle illumination has been proposed for sectioning in the context of fluorescence imaging, Unfortunately, in the case of a coherent imaging modality it does not work. In this embodiment, the method 1000 and system 100 combines broadband frequency swept speckle illumination through the sclera 154 and coherent detection of reflected light emerging through the pupil 152 using concepts of coherence gating techniques (e.g., interfering the reflected light with a reference in full-field, much like in full-field OCT). In analogy with Fourier Domain or Spectral Domain OCT, it is possible to scan the wavelength of the illumination or separate the wavelength before the detection and recover various interferograms to retrieve 3D information. Accordingly, it is possible to select a given imaging plane, and obtain an en face reflectivity image 105 of the ocular fundus 106, at the chosen depth. Compared to conventional OCT, however, one achieves higher resolution capability thanks to the structured nature of the speckle. Importantly, by utilizing a sweeping source 122, the system 100 avoids the contrast loss of the illumination speckle, and the need of compromising between sectioning capability (linked to spectral bandwidth) and resolution capability (limited by speckle contrast).

Figure 5:
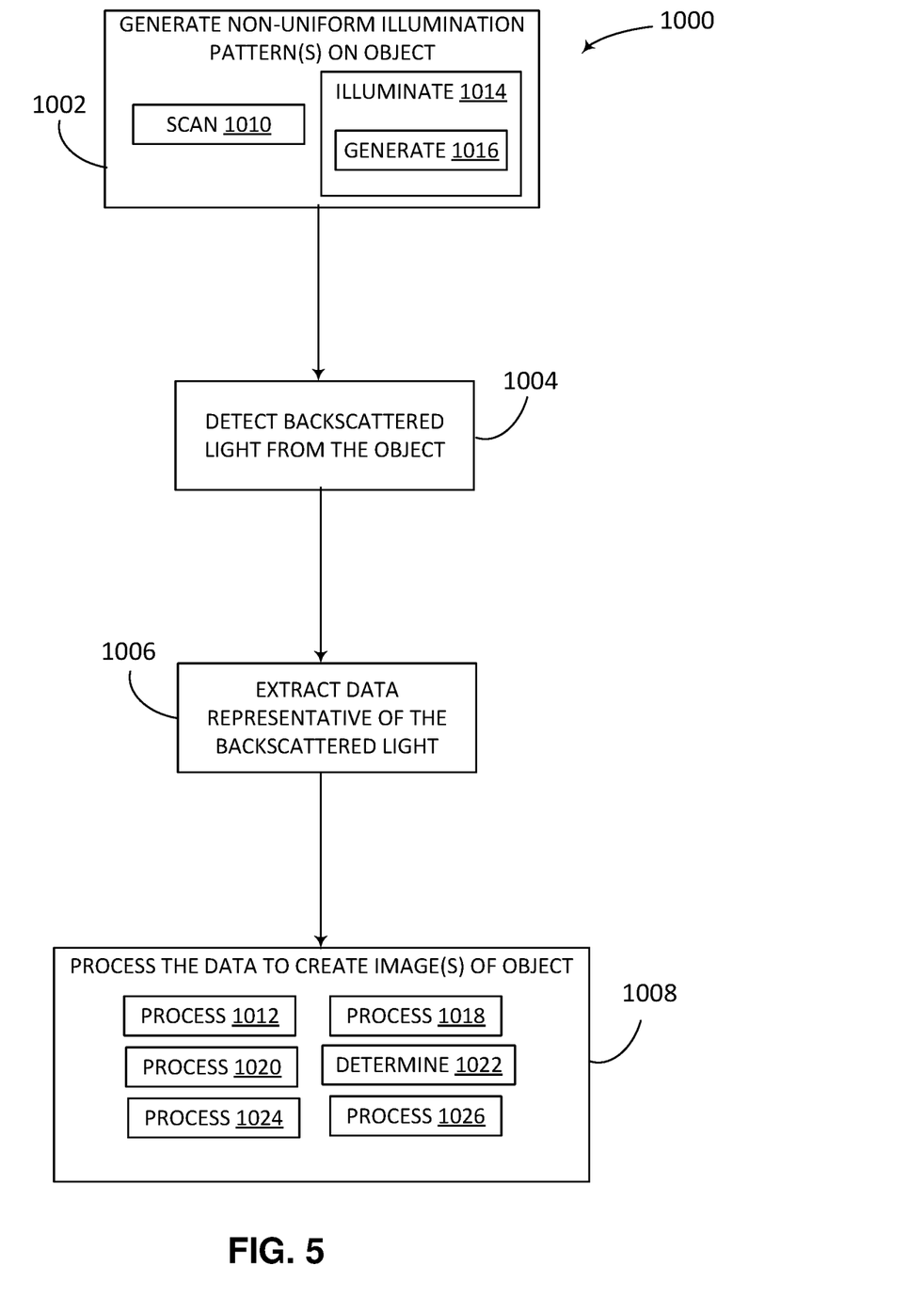
FIG. 5 is a flowchart diagram of a method for characterizing at least a portion of an object, according to an embodiment of the present technology.

FIG. 5 is a flowchart diagram of a method 1000 for characterizing at least a portion of an object, according to an embodiment of the present technology. The object in method 1000 can be an ocular structure of the eye. It is expected to be within the ready grasp and understanding of a person having ordinary skill in the art that method 1000 can be readily applied to objects other than eyes or ocular structures for which characterization according to the present technology is applicable and advantageous. Method 1000 may include the step of generating 1002, using at least one light source, one or multiple non-uniform illumination patterns on an object. The light source(s) used in method 1000 may include a laser. Method 1000 may also include the step of detecting 1004, using a detector, backscattered light from the object in response to the generating. Method 1000 may further include the step of extracting 1006, using the detector, data representative of the backscattered light. Method 1000 may also include the step of processing 1008, using a processing unit, the data representative of the backscattered light to create one or more images of at least a portion of the object. In an example, the generating 1002 step of method 1000 may include the step of scanning 1010, using the at least one light source, the one or multiple non-uniform illumination patterns over the object.

In one example, the one or multiple non-uniform illumination patterns provided in method 1000 for the generating 1002 step may include at least one speckle pattern. In this example, the processing 1008 step of method 1000 may include the step processing 1012 the data representative of the backscattered light using one or more algorithms for blind speckle-structured-illumination.

In another example, the generating 1002 step of method 1000 may include the step of illuminating 1014 at least a portion of the object with light of at least two different colors. In this example, the illuminating 1014 step in method 1000 may include the step of generating 1016 at least two different speckle patterns including: a first speckle pattern of a first color of light, and at least a second speckle pattern of at least a second color of light.

In yet another example, the processing 1008 step of method 1000 may include the step of processing 1018 the data representative of the backscattered light to generate: one or more depth images, or one or more optical sections, of the at least a portion of the object. In still another example, the processing 1008 step of method 1000 may include the step of processing 1020 the data representative of the light backscattering to characterize at least one aberration of, on, or in, the object. In another example, the processing 1008 step of method 1000 may include the step of determining 1022 at least one of: illumination, and at least one aberration, of the object.

In a further example of method 1000, the processing 1008 step of method 1000 may include processing 1024 the data representative of the light backscattering (or data derived or extracted therefrom) using one or more of: an optimization algorithm, a gradient descent algorithm, a convex optimization, a simulated annealing algorithm, a maximum likelihood estimation, a Bayesian estimation, a neural network, and a machine learning optimization. In yet another example, the processing 1008 step of method 1000 may include processing 1026 the data representative of the light backscattering (or data derived or extracted therefrom) using at least one of: a regularization process, a Tichonov regularization, a sparsity constraint, a nuclear norm constraint, a mean-constrained, a least absolute shrinkage and selection operator regularization, a total variation regularization, and a basis pursuit.

Figure 6:
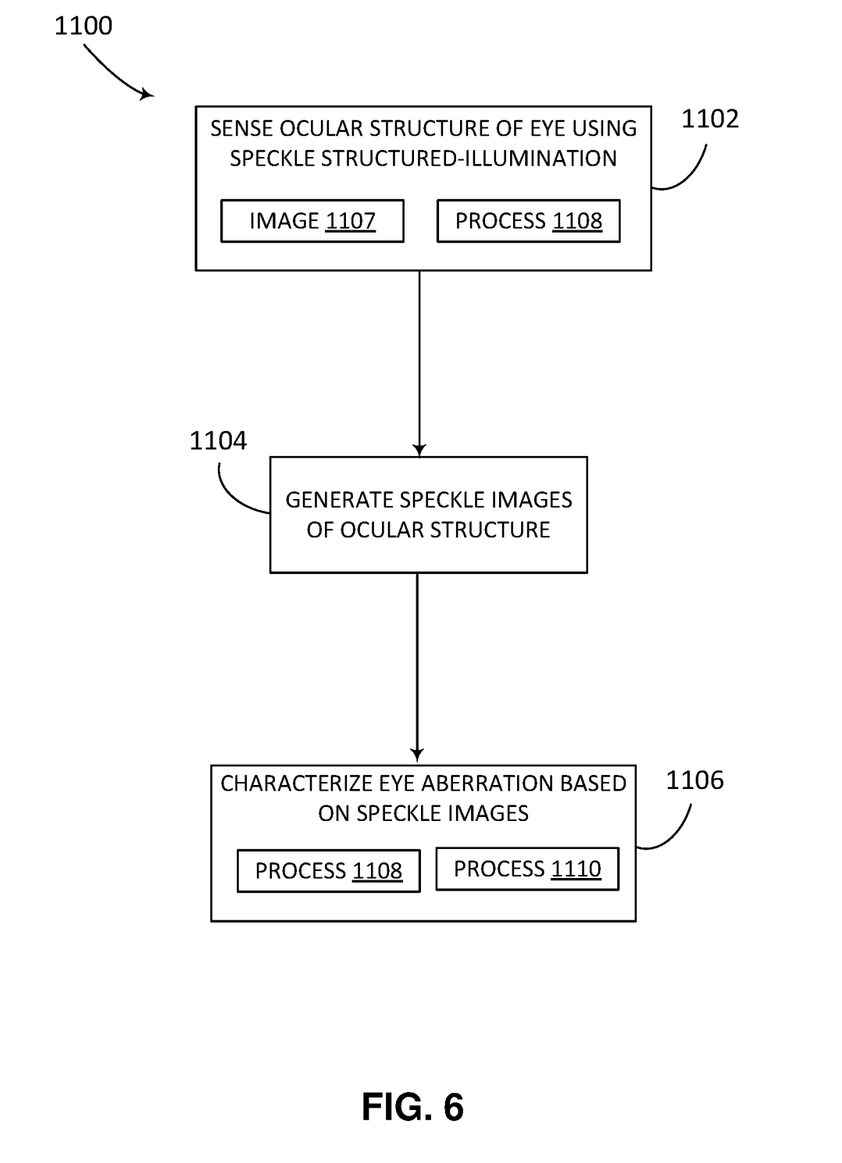
FIG. 6 is a flowchart diagram of a method for characterizing at least a portion of an ocular structure of the eye, according to an embodiment of the present technology.

FIG. 6 is a flowchart diagram of a method 1100 for characterizing at least a portion of an ocular structure of the eye, according to an embodiment of the present technology. It is expected to be within the ready grasp and understanding of a person having ordinary skill in the art that method 1100 can be readily applied to objects other than eye ocular structures for which characterization according to the present technology is applicable and advantageous. Method 1100 may include the step of sensing 1102 an ocular structure of an eye using speckle structured-illumination to generate 1104 speckle images of at least a portion of the ocular structure. Method 1100 may also include the step of characterizing 1106 an eye aberration based on the speckle images. In one example of method 1100, the sensing 1102 step may include the step of imaging 1107 the ocular structure.

In another example of method 1100, at least one of: the sensing 1102 step, and the characterizing 1106 step, may include the step of processing 1108 data representative of detected light emanating from the eye as a result of one or more of: scattering, reflection, absorption, fluorescence, two-photon excitation, and high harmonic generation. In this example, the processing 1108 step of method 1100 may include the step of processing 1110 the data representative of detected light emanating from the eye using one or more algorithms for blind speckle-structured-illumination.

Figure 7:
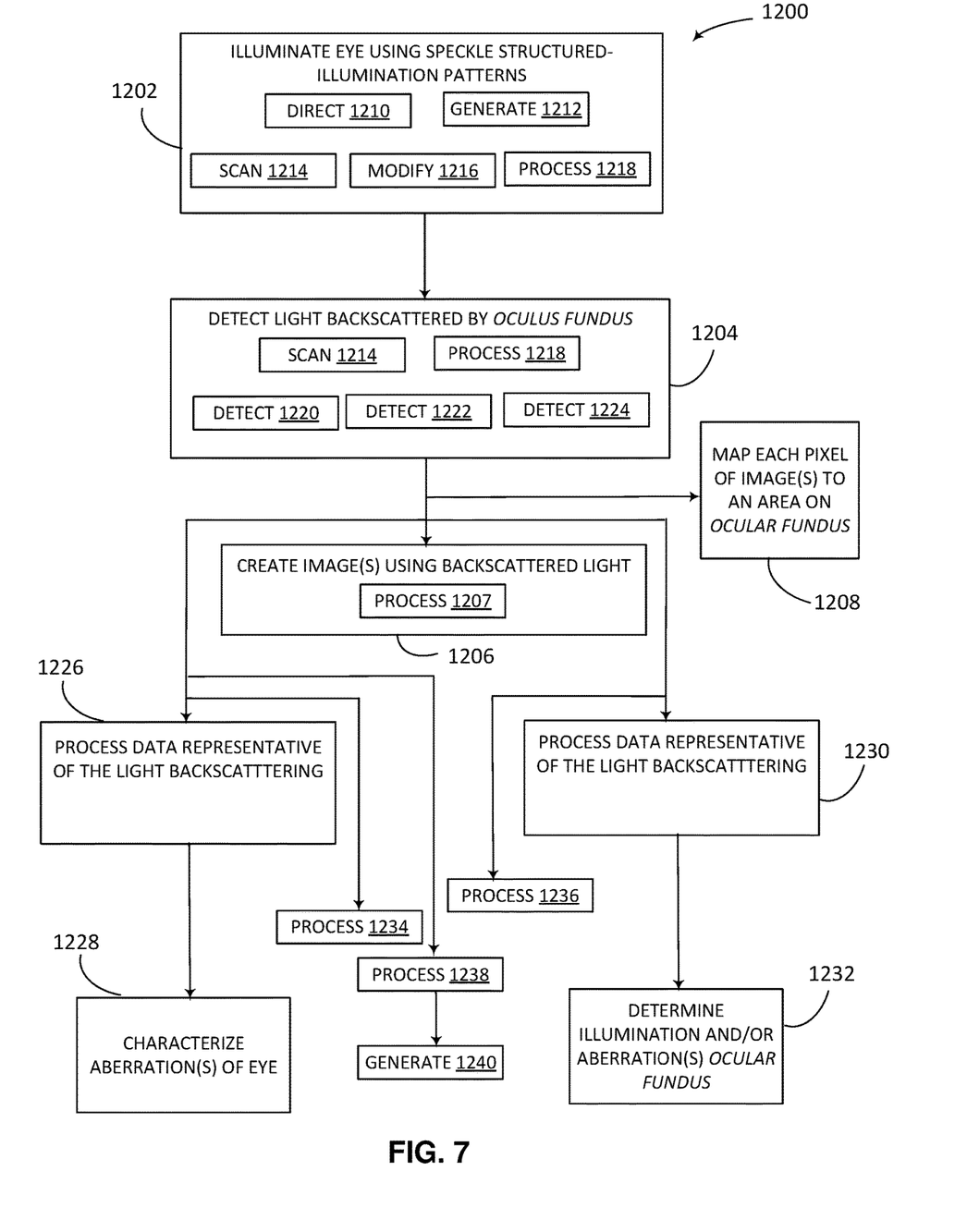
FIG. 7 is a flowchart diagram of a method for characterizing at least a portion of an eye, according to an embodiment of the present technology.

FIG. 7 is a flowchart diagram of a method 1200 for characterizing at least a portion of an eye, according to an embodiment of the present technology. It is expected to be within the ready grasp and understanding of a person having ordinary skill in the art that method 1200 can be readily applied to objects other than portion(s) of the eye for which characterization according to the present technology is applicable and advantageous. Method 1200 may include the step of illuminating 1202 an eye using one or multiple speckle structured-illumination patterns. Method 1200 may also include the step of detecting 1204 light backscattered by an ocular fundus of the eye in response to the illuminating 1202. Method 1200 may further include the step of creating 1206 one image or a series of images using the light backscattered by the ocular fundus. The creating 1206 step of method 1200 may include the step of processing 1207 the one image or the series of images to generate at least one super-resolution image of at least a portion of the oculus fundus.

In one example of method 1200, one or both of: the illuminating 1202 step, and the detecting 1204 step, is implemented trans-pupillary or trans-scleral. In another example, method 1200 may additionally include the step of mapping 1208 each pixel of the image or series of images to an area on the ocular fundus. In yet another example, the illuminating 1202 step of method 1200 may include the step of directing 1210 laser light (or light from other source(s)) through a scattering medium to generate 1212 a speckle pattern on the ocular fundus. In this example of method 1200, one or both of: the illuminating 1202 step, and the detecting 1204 step, may include the step of scanning 1214 the speckle pattern over at least a portion of the ocular fundus. Also, in this example, method 1200 may include the step of modifying 1216 the speckle pattern over time. Furthermore, in this example of method 1200, at least one of the: illuminating 1202, and detecting 1204, steps may include the step of processing 1218 data representative of the light backscattering using one or more algorithms for blind speckle-structured-illumination.

In yet another example, the detecting 1204 step of method 1200 may include at least one of the following steps: detecting 1220 light that is reflected from the ocular fundus, and detecting 1222 light resulting from fluorescence from intrinsic or extrinsic substances in or on the ocular fundus. In still another example, the detecting 1204 step of method 1200 may include detecting 1224 light emanating from the eye as a result of one or more of: scattering, reflection, absorption, fluorescence, two-photon excitation, and high harmonic generation.

In still another example, method 1200 may further include the step of processing 1226 data representative of the light backscattering to characterize 1228 at least one aberration of the eye. In another example, method 1200 may also include the step of processing 1230 the data representative of the light backscattering to determine 1232 at least one of: illumination, and at least one aberration, of the ocular fundus or other portion(s) of the eye.

In yet another example, method 1200 may further include the step of processing 1234 data representative of the light backscattering (or data derived or extracted therefrom) using one or more of: an optimization algorithm, a gradient descent algorithm, a convex optimization, a simulated annealing algorithm, a maximum likelihood estimation, a Bayesian estimation, a neural network, and a machine learning optimization. In still another example, method 1200 may include the step of processing 1236 the data representative of the light backscattering (or data derived or extracted therefrom) using at least one of: a regularization process, a Tichonov regularization, a sparsity constraint, a nuclear norm constraint, a mean-constrained, a least absolute shrinkage and selection operator regularization, a total variation regularization, and a basis pursuit. In another example, method 1200 may also include the step of processing 1238 the data representative of the light backscattered by the ocular fundus to generate 1240: one or more depth images, or one or more optical sections, of at least a portion of the oculus fundus.

CONCLUSION

Unless the context clearly requires otherwise, throughout the description and the claims, the words "comprise," "comprising," and the like are to be construed in an inclusive sense, as opposed to an exclusive or exhaustive sense; that is to say, in the sense of "including, but not limited to." As used herein, the terms "connected," "coupled," or any variant thereof means any connection or coupling, either direct or indirect, between two or more elements; the coupling or connection between the elements can be physical, logical, or a combination thereof. Additionally, the words "herein," "above," "below," and words of similar import, when used in this application, refer to this application as a whole and not to any particular portions of this application. Where the context permits, words in the above Detailed Description using the singular or plural number may also include the plural or singular number respectively. The word "or," in reference to a list of two or more items, covers all of the following interpretations of the word: any of the items in the list, all of the items in the list, and any combination of the items in the list.

The above Detailed Description of examples of the technology is not intended to be exhaustive or to limit the technology to the precise form disclosed above. While specific examples for the technology are described above for illustrative purposes, various equivalent modifications are possible within the scope of the technology, as those skilled in the relevant art will recognize. For example, while processes or blocks are presented in a given order, alternative implementations may perform routines having steps, or employ systems having blocks, in a different order, and some processes or blocks may be deleted, moved, added, subdivided, combined, and/or modified to provide alternative or subcombinations. Each of these processes or blocks may be implemented in a variety of different ways. Also, while processes or blocks are at times shown as being performed in series, these processes or blocks may instead be performed or implemented in parallel, or may be performed at different times. Further any specific numbers noted herein are only examples: alternative implementations may employ differing values or ranges.

The teachings of the technology provided herein can be applied to other systems, not necessarily the system described above. The elements and acts of the various examples described above can be combined to provide further implementations of the technology. Some alternative implementations of the technology may include not only additional elements to those implementations noted above, but also may include fewer elements.

These and other changes can be made to the technology in light of the above Detailed Description. While the above description describes certain examples of the technology, and describes the best mode contemplated, no matter how detailed the above appears in text, the technology can be practiced in many ways. Details of the system may vary considerably in its specific implementation, while still being encompassed by the technology disclosed herein. As noted above, particular terminology used when describing certain features or aspects of the technology should not be taken to imply that the terminology is being redefined herein to be restricted to any specific characteristics, features, or aspects of the technology with which that terminology is associated.

In general, the terms used in the following claims should not be construed to limit the technology to the specific examples disclosed in the specification, unless the above Detailed Description section explicitly defines such terms. Accordingly, the actual scope of the technology encompasses not only the disclosed examples, but also all equivalent ways of practicing or implementing the technology under the claims.

To reduce the number of claims, certain aspects of the technology are presented below in certain claim forms, but the applicant contemplates the various aspects of the technology in any number of claim forms. For example, while only one aspect of the technology is recited as a computer-readable medium claim, other aspects may likewise be embodied as a computer-readable medium claim, or in other forms, such as being embodied in a means-plus-function claim. Any claims intended to be treated under 35 U.S.C. § 112(f) will begin with the words "means for", but use of the term "for" in any other context is not intended to invoke treatment under 35 U.S.C. § 112(f). Accordingly, the applicant reserves the right to pursue additional claims after filing this application to pursue such additional claim forms, in either this application or in a continuing application.

What is claimed is:

1. A system comprising:
    at least one light source to generate two or more non-uniform illumination patterns on an object, wherein the at least one light source is configured to illuminate at least a portion of the object with:
    light of at least two colors; and
    at least two different speckle patterns comprising a first speckle pattern of a first color of light and at least a second speckle pattern of at least a second color of light, wherein the two or more non-uniform illumination patterns comprise the two different speckle patterns;
    a detector array to extract data representing backscattering from the object; and
    a processing unit configured to:
        receive the data representing backscattering from the object; and
        generate one or more images of at least a portion of the object.

2. The system of claim 1, wherein the at least one light source is configured to scan the two or more non-uniform illumination patterns over the object.

3. The system of claim 1, wherein the two or more non-uniform illumination patterns include at least one additional speckle pattern.

4. The system of claim 3, wherein the processing unit is further configured to process the data representing backscattering from the object using one or more algorithms for blind speckle-structured-illumination.

5. The system of claim 1, wherein the at least one light source includes a laser.

6. The system of claim 1, wherein the processing unit is further configured to process the data representing backscattering from the object to generate: one or more depth images, or optical sections, of the at least a portion of the object.

7. The system of claim 1, wherein the processing unit is further configured to process the data representing backscattering from the object to characterize at least one aberration of the object.

8. The system of claim 1, wherein the processing unit is further configured to process the data representing backscattering from the object to determine at least one of: illumination, and at least one aberration, of the object.

9. The system of claim 1, wherein the processing unit is further configured to process the data representing backscattering from the object using one or more of:
    an optimization algorithm, a gradient descent algorithm, a convex optimization, a simulated annealing algorithm, a maximum likelihood estimation, a Bayesian estimation, a neural network, and a machine learning optimization.

10. The system of claim 1, wherein the processing unit is further configured to process the data representing backscattering from the object using at least one of: a regularization process, a Tichonov regularization, a sparsity constraint, a nuclear norm constraint, a mean-constrained, a least absolute shrinkage and selection operator regularization, a total variation regularization, and a basis pursuit.

11. The system of claim 1, wherein the object is an ocular structure of an eye.

12. The system of claim 1, wherein:
    the object includes an eye or an ocular structure;
    the detector array is configured to collect backscattered, or fluorescence, light from the eye or the ocular structure;
    a mask to isolate an illumination path and a detection path; and
    the processing unit is further configured to:
        receive data representing the backscattering, or fluorescent, light; and
        generate one or more images of the eye or the ocular structure.

13. The system of claim 12, further comprising a mask to isolate an illumination path and a detection path.

14. The system of claim 13, wherein the mask includes:
    a binary mask; or
    a binary mask including a spoke-wheel mask.

15. The system of claim 13, wherein an isolation, by the mask, of the illumination path and the detection path facilitates maximizing a numerical aperture.

* * * * *

UNITED STATES PATENT AND TRADEMARK OFFICE
CERTIFICATE OF CORRECTION

Page 1 of 1

PATENT NO. : 12,379,312 B2
APPLICATION NO. : 17/765364
DATED : August 5, 2025
INVENTOR(S) : Rafael Piestun et al.

It is certified that error appears in the above-identified patent and that said Letters Patent is hereby corrected as shown below:

On the Title Page

Item (71), Applicants, after "The Regents of the University of Colorado," add --a body corporate,--

Item (73), Assignees, after "The Regents of the University of Colorado," add --a body corporate,--

Signed and Sealed this
Seventh Day of October, 2025

John A. Squires
*Director of the United States Patent and Trademark Office*